(12) United States Patent
Longley et al.

(10) Patent No.: US 11,998,407 B2
(45) Date of Patent: *Jun. 4, 2024

(54) METHODS OF PRODUCING REMOVABLE ORAL DEVICES

(71) Applicant: SCIENTIFIC INTAKE LIMITED CO., Lawrence, MA (US)

(72) Inventors: William H Longley, Atlanta, GA (US); Richard P Schneider, Bedford, NY (US); Anthony R Tremaglio, Waban, MA (US); Marc M Gibeley, Boxford, MA (US)

(73) Assignee: SCIENTIFIC INTAKE LIMITED CO., Atlanta, GA (US)

( * ) Notice: Subject to any disclaimer, the term of this patent is extended or adjusted under 35 U.S.C. 154(b) by 421 days.

This patent is subject to a terminal disclaimer.

(21) Appl. No.: 17/352,415

(22) Filed: Jun. 21, 2021

(65) Prior Publication Data

US 2022/0142751 A1    May 12, 2022

Related U.S. Application Data

(63) Continuation of application No. 15/702,554, filed on Sep. 12, 2017, now abandoned.
(Continued)

(51) Int. Cl.
*A61C 13/00* (2006.01)
*A61C 7/00* (2006.01)
(Continued)

(52) U.S. Cl.
CPC .......... *A61C 13/0004* (2013.01); *A61C 7/002* (2013.01); *A61C 7/10* (2013.01);
(Continued)

(58) Field of Classification Search
CPC ......... A61F 5/00–0006; A61F 5/56–58; A61B 5/0002; A61B 5/0015; A61B 5/0017; A61B 5/0059; A61B 5/0077; A61B 5/0088; A61B 5/01; A61B 5/05; A61B 5/053; A61B 5/0537; A61B 5/08; A61B 5/082; A61B 5/083–0836; A61B 5/48; A61B 5/4836; A61B 5/68; A61B 5/6801; A61B 5/6802; A61B 5/6813; A61B 5/6814; A61B 5/682; A61B 2503/00; A61B 2503/10; A61B 2562/00; A61B 2562/02; A61B 2562/0219; A61B 2562/0247; A61B 13/00;
(Continued)

(56) References Cited

U.S. PATENT DOCUMENTS 5,924,422 A * 7/1999 Gustafson ............. A61F 5/0006
                                                                                        128/846
7,182,596 B2 * 2/2007 Paulus ...................... A61C 7/10
                                                                                         433/21

FOREIGN PATENT DOCUMENTS

WO    WO-2017006176 A1 *   1/2017   ........... A44C 15/007

* cited by examiner

*Primary Examiner* — Michelle J Lee
(74) *Attorney, Agent, or Firm* — Rhodes IP PLC; Christopher Rhodes

(57) ABSTRACT

Certain configurations of methods which can be used to produce removable oral devices are described. In some instances, the removable oral devices can be produced using molding, digital scanning, on demand printing and/or other processes. In certain examples, the produced removable oral device can be used in weight management, athletic performance or in other applications.

15 Claims, 5 Drawing Sheets

Related U.S. Application Data

(60) Provisional application No. 62/521,498, filed on Jun. 18, 2017, provisional application No. 62/477,764, filed on Mar. 28, 2017.

(51) Int. Cl.
*A61C 7/10* (2006.01)
*A61F 5/00* (2006.01)
*B33Y 40/20* (2020.01)
*A61C 9/00* (2006.01)

(52) U.S. Cl.
CPC ........ *A61C 13/0006* (2013.01); *A61F 5/0006* (2013.01); *B33Y 40/20* (2020.01); *A61C 9/0046* (2013.01); *A61C 13/0013* (2013.01); *A61C 13/0022* (2013.01)

(58) Field of Classification Search
CPC .... A61B 1/00; A61B 1/24; A61C 7/00; A61C 7/08; A61C 7/10; A61C 7/36; A61C 19/06–08; A61C 13/0003–0006; A61C 13/0013; A61C 13/0002; A61C 7/002; A61C 9/00; A61C 9/004; A61C 9/0046; A63B 71/08–085; A63B 2071/086; A63B 2071/088; A61M 16/0488–0497; B33Y 40/20

See application file for complete search history.

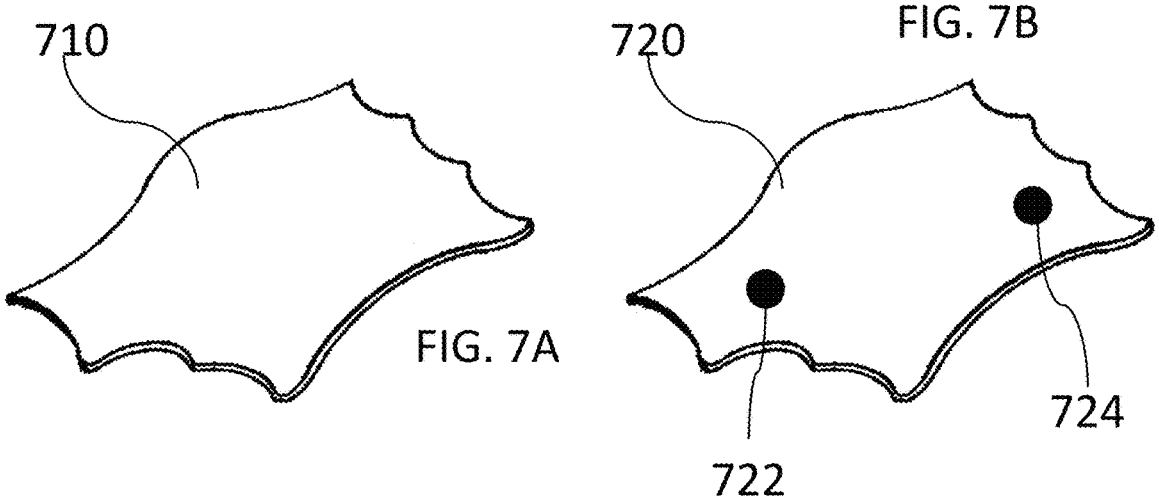
FIG. 7A
FIG. 7B
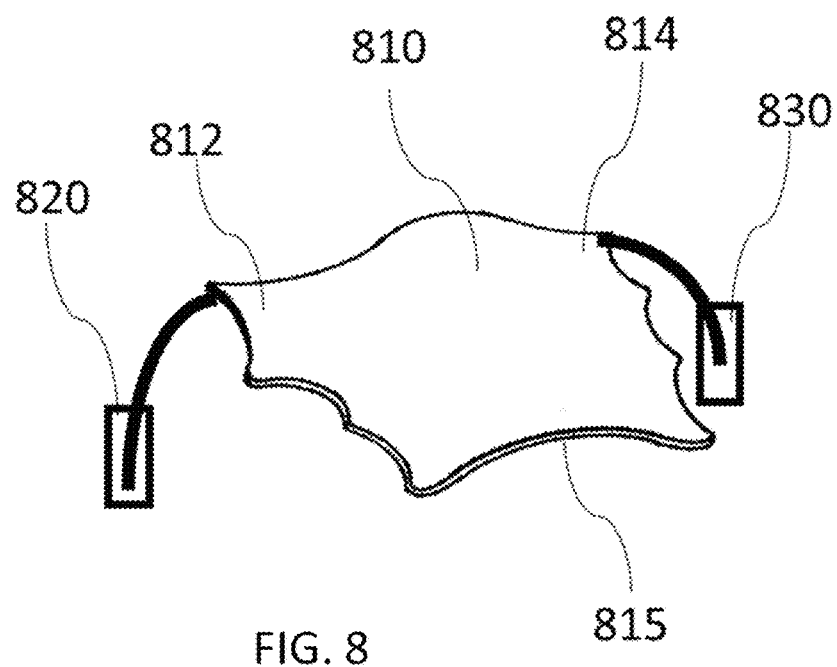
FIG. 8
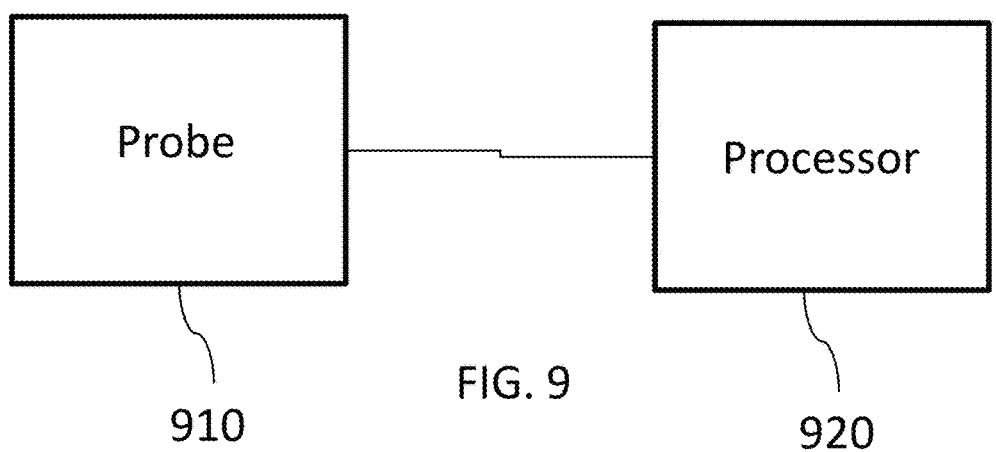
FIG. 9

METHODS OF PRODUCING REMOVABLE ORAL DEVICES

PRIORITY APPLICATIONS

This application claims priority to and the benefit of U.S. 62/477,764 filed on Mar. 28, 2017 and entitled "METHODS OF PRODUCING REMOVABLE ORAL DEVICES" and claims priority to U.S. Provisional Application No. 62/521,498 filed on Jun. 18, 2017 and entitled "METHODS OF USING REMOVABLE ORAL DEVICES." The entire disclosure of each of these applications is hereby incorporated herein by reference for all purposes.

CROSS-REFERENCE TO RELATED APPLICATIONS

This application is related to, and incorporates by reference herein, each of the following patent applications: U.S. Provisional Application 62/477,752 filed on Mar. 28, 2017 and entitled "REMOVABLE ORAL DEVICES," U.S. Provisional Application 62/477,760 filed on Mar. 28, 2017 and entitled "METHODS OF USING REMOVABLE ORAL DEVICES," U.S. Provisional Application 62/477,766 filed on Mar. 28, 2017 and entitled "SYSTEMS INCLUDING REMOVABLE ORAL DEVICES," and U.S. Provisional Application 62/477,768 filed on Mar. 28, 2017 and entitled "REMOVABLE ORAL DEVICES AND THEIR USE IN COMBINATION WITH PHARMACOLOGICAL AGENTS, IMPLANTS AND OTHER DEVICES."

TECHNOLOGICAL FIELD

This application is directed to methods of producing removable oral devices. More particularly, certain configurations described herein are directed to methods of producing removable oral devices using molding, digital scanning, on demand printing and/or other suitable techniques.

BACKGROUND

Many methods for controlling weight exist. Most existing methods do not provide long term weight loss or health benefits.

SUMMARY

Certain illustrative configurations are directed to various methods which can be used to produce removable oral devices that can be inserted into the mouth. As noted in more detail below, the methods can permit production of a customized removable oral device of various configurations that can be used for various end uses.

In one aspect, a method of producing a removable oral device comprises printing, e.g., three-dimensionally printing, a removable oral device using a first material. In some examples, the printed removable oral device comprises a palatal element coupled to an optional clasping element. In certain instances, the palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the mouth and/or to retain the palatal surface of the palatal element against the roof of the user's mouth when the removable oral device is inserted into the user's mouth.

In certain configurations, the method comprises printing areas of the body adjacent to the clasping element using a second material softer than the first material.

In other configurations, the method comprises three-dimensionally printing the palatal element using a photo-curable material.

In some examples, the method comprises disposing one or more wires on a printer support as the clasping element and printing the photo-curable material into the printer support comprising the one or more wires to provide the removable oral device.

In some embodiments, the method comprises photo-curing the printed palatal element using UV/Visible light.

In some configurations, the method comprises printing each of the palatal element and the clasping element using a photo-curable material.

In other examples, the method comprises three-dimensionally printing the removable oral device using an inkjet three-dimensional printer.

In some examples, the method comprises three-dimensionally printing the removable oral device using digital light processing.

In further examples, the method comprises three-dimensionally printing the removable oral device from a digital image of the user's mouth.

In other examples, the method comprises three-dimensionally printing the palatal element of the digital image using a photo-curable material.

In some examples, the method comprises disposing one or more wires on a printer support as the clasping element and printing the photo-curable material onto the printer support comprising the one or more disposed wires to provide the removable oral device.

In certain configurations, the method comprises configuring the removable oral device to not alter a position of the user's teeth.

In other configurations, the method comprises configuring the removable oral device to not retain a position of the user's teeth.

In another aspect, a method comprising imaging an oral cavity of a human, and providing a removable oral device from the imaged oral cavity is described. For example, the provided removable oral device comprises a palatal element coupled to an optional clasping element. In some instances, the palatal element is configured to contact a roof of a user's mouth at a palatal surface. In some examples, the palatal element comprises a body comprising a thickness configured to lower a vaulted area of the roof of the mouth to decrease an overall oral volume of the mouth to a first oral volume. If desired, the palatal element may comprise a variable hardness. In some examples where a clasping element is present, the clasping element is configured to assist in removal of the removable oral device from the mouth.

In certain examples, the method comprises producing the removable oral device with areas of the body adjacent to the clasping element being softer than other areas of the body.

In some examples, the method comprises imaging the oral cavity using an image head electrically coupled to a wireless device.

In other examples, the method comprises imaging the oral cavity using a probe configured to capture ultrasound images of the oral cavity.

In some embodiments, the method comprises imaging the oral cavity using a probe configured to capture still images of the oral cavity.

In other embodiments, the method comprises imaging the oral cavity using a probe configured to capture video images of the oral cavity.

In further embodiments, the method comprises wirelessly transmitting images from the probe to a mobile device.

In certain examples, the method comprises using the image of the oral cavity to print a removable oral device.

In some embodiments, the method comprises printing the removable oral device using three-dimensional printing.

In other embodiments, the method comprises configuring the removable oral device to not alter a position of the user's teeth.

In some examples, the method comprises configuring the removable oral device to not retain a position of the user's teeth.

In an additional aspect, a method comprises obtaining an impression of an oral cavity of a human using an impression tray and impression material, and providing a removable oral device using the impression of the oral cavity. For example, the removable oral device may comprise a palatal element coupled to an optional clasping element. In some examples, the palatal element is configured to contact a roof of a user's mouth at a palatal surface and may comprise a body comprising a thickness configured to lower a vaulted area of the roof of the mouth to decrease an overall oral volume of the mouth to a first oral volume. In some instances, the body comprises a variable hardness across a tongue surface of the body, e.g., can be softer at the edges than at an apex area. In examples where a clasping element is present, the clasping element can be configured to assist in removal of the removable oral device from the mouth.

In certain examples, the method comprises printing the impression tray using a three-dimensional printer.

In other examples, the method comprises using an image of the oral cavity in combination with the impression of the oral cavity to provide a composite image.

In some embodiments, the method comprises printing the palatal element from the composite image using a three-dimensional printer.

In certain examples, the method comprises configuring edges of the palatal element to be softer than an apex of the palatal element.

In other examples, the method comprises configuring the removable oral device to not alter a position of the user's teeth.

In another aspect, a method comprises imaging an oral cavity of a human, and providing a removable oral device from the imaged oral cavity. For example, the provided removable oral device comprises a palatal element coupled to a clasping element. The palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the mouth and/or to retain the palatal surface of the palatal element against the roof of the user's mouth when the removable oral device is inserted into the user's mouth.

In an additional aspect, a method comprises imaging an oral cavity of a human using an image head configured to receive a disposable cover, and printing a removable oral device from the imaged oral cavity using a first material. In some examples, the printed removable oral device comprises a palatal element coupled to a clasping element. The palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the mouth and/or to retain the palatal surface of the palatal element against the roof of the user's mouth when the removable oral device is inserted into the user's mouth.

In another aspect, the imaging of the oral cavity may be performed using an external imager which can be placed adjacent to or near the teeth. The images from the external imager can be used to print or otherwise provide a removable oral device as described herein.

In another aspect, a method comprises imaging an oral cavity of a human, printing a mold from the imaged oral cavity, and using the printed mold to provide a removable oral device. In some examples, the removable oral device comprises a palatal element coupled to a clasping element. For example, the palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, is configured to assist in removal of the removable oral device from the mouth and/or to retain the palatal surface of the palatal element against the roof of the user's mouth when the removable oral device is inserted into the user's mouth.

In an additional aspect, a method comprises imaging an oral cavity of a human, printing an impression tray using the imaged oral cavity, using the printed impression tray and impression material to obtain an impression of the oral cavity of the human, and providing a removable oral device using the impression of the oral cavity. In some embodiments, the removable oral device comprises a palatal element coupled to a clasping element. For example, the palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, is configured to assist in removal of the removable oral device from the mouth and/or to retain the palatal surface of the palatal element against the roof of the user's mouth when the removable oral device is inserted into the user's mouth.

In another aspect, a method comprises obtaining an impression of an oral cavity of a human using an impression tray and impression material, and providing a removable oral device using the impression of the oral cavity. In some instances, the removable oral device comprises a palatal element coupled to a clasping element. In some embodiments, the palatal element is configured to contact a roof of a user's mouth at a palatal surface. In certain examples, the palatal element comprises a body comprising a thickness configured to lower a vaulted area of the roof of the mouth to decrease an overall oral volume of the mouth to a first oral volume, wherein the body comprises a variable hardness across a tongue surface of the body. The clasping element, when present, can be configured to assist in removal of the removable oral device from the mouth and/or to retain the palatal surface of the palatal element against the roof of the user's mouth when the removable oral device is inserted into the user's mouth.

In an additional aspect, a method comprises imaging an oral cavity of a human using a first removable oral device comprising a palatal element coupled to a clasping element, in which the palatal element of the first removable oral device comprises a body comprising an embedded camera configured to capture an image of the oral cavity. The clasping element of the first removable oral device, when present, can be configured to assist in removal of the first removable oral device from the mouth when the first removable oral device is inserted into the human's mouth. The method may also comprise using the captured image to provide a second removable oral device comprising a palatal element coupled to a clasping element. The palatal element of the second removable oral device can be configured to contact a roof of a user's mouth at a palatal surface. The palatal element of the second removable oral device comprises a body comprising a thickness configured to lower a vaulted area of the roof of the mouth to decrease an overall oral volume of the mouth to a first oral volume. The clasping element of the second removable oral device, when present, can be configured to assist in removal of the second removable oral device from the mouth and/or to retain the palatal surface of the palatal element of the second removable oral device against the roof of the user's mouth when the second removable oral device is inserted into the user's mouth.

In another aspect, a method comprises imaging an oral cavity of a human using a first removable oral device comprising a palatal element coupled to a clasping element, in which the palatal element of the first removable oral device comprises a body comprising an embedded sensor configured to map the oral cavity, and wherein the clasping element of the first removable oral device is configured to assist in removal of the first removable oral device from the mouth when the first removable oral device is inserted into the human's mouth. In some examples, the method also comprises using the captured image to provide a second removable oral device comprising a palatal element coupled to a clasping element. The palatal element of the second removable oral device can be configured to contact a roof of a user's mouth at a palatal surface. The palatal element of the second removable oral device comprises a body comprising a thickness configured to lower a vaulted area of the roof of the mouth to decrease an overall oral volume of the mouth to a first oral volume. The clasping element of the second removable oral device, when present, is configured to assist in removal of the second removable oral device from the mouth and/or to retain the palatal surface of the palatal element against the roof of the user's mouth when the second removable oral device is inserted into the user's mouth.

In an additional aspect, a method of producing a removable oral device comprises providing a removable oral device comprising a palatal element coupled to a clasping element, in which the palatal element is configured to contact a roof of a user's mouth at a palatal surface. The palatal element comprises a body comprising a thickness configured to lower a vaulted area of the roof of the mouth to decrease an overall oral volume of the mouth to a first oral volume. The palatal element comprises a softer material at edges of the body than at an apex of the body. The clasping element, when present, can be configured to assist in removal of the removable oral device from the mouth and/or to retain the palatal surface of the palatal element against the roof of the user's mouth when the removable oral device is inserted into the user's mouth. The method may also comprise forming the clasping element by bending the clasping element and sizing it to contact outer surfaces of at least one, two or three teeth.

Additional aspects, examples, embodiments and configurations are described further below.

BRIEF DESCRIPTION OF THE SEVERAL VIEWS OF THE DRAWINGS

Certain configurations of methods of producing removable oral devices are described below with reference to the accompanying figures in which:

FIGS. 7A and 7B are illustrations of a stackable/couplable palatal elements in accordance with certain examples;

FIG. 8 is an illustration of a removable oral device, in accordance with certain examples;

FIG. 9 is a schematic of a system for imaging an oral cavity, in accordance with certain configurations.

DETAILED DESCRIPTION

Various components are described below in connection with methods which can be used to produce a removable oral device. The exact number and ordering of the steps may vary depending on the device to be produced, the production environment and the materials used. The processes and materials provided below are merely illustrative of many steps, materials and conditions which can be used. Further, a clasping element can be present or can be omitted from the removable oral device as desired.

In certain embodiments, the removable oral devices described herein typically comprise a palatal element and an optional clasping element. The palatal element can be configured to contact a roof of a user's mouth at a palatal surface and may comprise a body comprising a thickness configured to lower a vaulted area of the roof of the mouth to decrease an overall oral volume of the mouth to a first oral volume. As noted in more detail herein, different areas of the clasping element may comprise different materials and/or a different hardness as desired. The clasping element can perform one or more functions including, for example, facilitating removal of the removable oral device from the mouth and/or assisting in retention of the palatal surface of the palatal element against the roof of the user's mouth when the removable oral device is inserted into the user's mouth. Various methods of producing such removable oral devices are described below.

Figure 1:
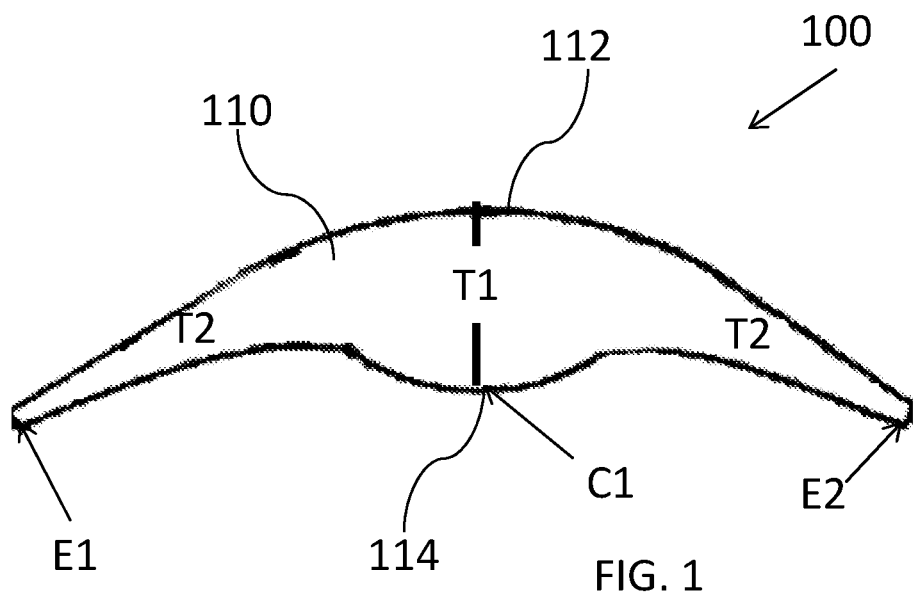
FIG. 1 is a side view of a palatal element of a removable oral device, in accordance with certain examples.

In certain examples, FIG. 1 shows a generalized illustration of one configuration of a palatal element of a removable oral device that can be produced using the methods described herein. The palatal element 100 comprises a body 110 comprising a palatal surface 112 and a tongue surface 114. Notwithstanding that many different methods and devices can be used to produce the palatal element 100, the palatal element 100 is generally designed so the palatal surface 112 conforms or contours to the roof of a user's mouth. A tongue surface 114 generally mirrors or replicates the roof or palate shape of the user. In some instances, the palatal element 100 has a thickness T1 (from the highest point or apex of the palatal surface 112 to the lowest point of the tongue surface 114) at a medial portion of the palatal element 100. The thickness T2 at an edge of the palatal element 100 is generally less than the thickness T1. For example, the portions of the palatal element 100 which sit against or are adjacent to the upper teeth are typically 2×, 3×, 4× or 5× less thick than the thickness T1 to provide a more comfortable fit in a user's mouth. As noted in more detail herein, the thickness T1 may be adjusted or adjustable as desired. Without wishing to be bound by any particular theory or configuration, the thickness T1 can be selected to decrease the overall oral volume of the mouth available for chewing and/or to better position one or more sensors of the palatal element 100 in an appropriate position. The amount by which the oral volume is reduced is controlled generally by the thickness T1 and may vary from user to user or depending on the particular disorder to be treated, the particular condition to be monitored, feedback received by application software or a coach and other criteria. While the exact reduction in volume can vary, in some examples, the thickness T1 is selected such that the oral volume is reduced by 5% to about 50% (as compared to an original oral volume where no removable oral device is present), more particularly reduced by about 15% to about 35% or about 25% to about 35%. As noted in more detail below, the thickness of the palatal element may be altered with increasing temperature, by coupling one or more additional palatal element bodies to the palatal element or by other means. For example, an expandable bladder, e.g., an air bladder or liquid bladder, can be present in the palatal element 100 to alter the overall volume of the palatal element 100.

In certain embodiments, the removable oral device comprising the palatal element 100 can be used to reduce the overall volume of the mouth to slow food intake. For example, the decrease in overall volume provided when the palatal element 100 is inserted into a user's mouth 100 permits smaller bites of food and/or lower overall food volume per bite to be introduced into the mouth, which can enhance mindful eating practices. This result can increase the overall time it takes to ingest a particular volume of food, which can promote increased satiety and an overall reduction in food intake volume, e.g., fewer overall calories are consumed when the removable oral device is present compared to the removable oral device not being inserted into a user's mouth.

In some instances, the removable oral device comprising the palatal element, e.g., one without a clasping element or one with a clasping element, can be used in weight management and/or weight control. For example, a user can insert the removable oral device prior to eating, e.g., once per day, twice per day, three times per day, once per week, five days per week, twice per week, every time a user ingests food, etc. to assist in weight management. As noted herein, when the removable oral device is in place, the overall level of calories ingested during a particular eating session can be reduced, which can result in weight loss and/or weight management. In addition, by forcing the user to chew a particular quantity of food for a longer period, mindful eating practices can be adopted through behavioral modification. In certain configurations, and as described in more detail in commonly assigned applications bearing application numbers U.S. 62/477,760 and U.S. 62/477,766, the removable oral device can be used in combination with a coaching platform or coaching based devices to provide feedback and/or monitoring of the user's use of the removable oral device and/or to assist in weight management. Such coaching platforms may take the form of in-person sessions, external sessions over a remote connection or automated sessions retrieved by the user through one or more software applications on a mobile device or other electronic device.

In some instances, the removable oral device comprising a palatal element can be used until a user's body fat percentage or body mass index (BMI) reaches a desired level. For example, the removable oral device can be used in weight management with people having a body mass index between 25 and 30. If desired, the removable oral device could also be used with people whose body mass index exceeds 30 or is under 25. In some examples, the removable oral device can be used with human males comprising a body fat percentage between 22-29% or exceeding 26% or with human females comprising a body fat percentage of 31-39% or exceeding 31%. In some examples, the removable oral device frequency can be reduced once the user's BMI or body fat percentage drops below a selected level, e.g., below a BMI of 25 or below a body fat percentage of 22% or 25% for human males and 31% for human females. For example, weight maintenance can be attained by using the removable oral device once per week or 2-3× per week rather than using the removable oral device daily to assist in weight loss.

Figure 2:
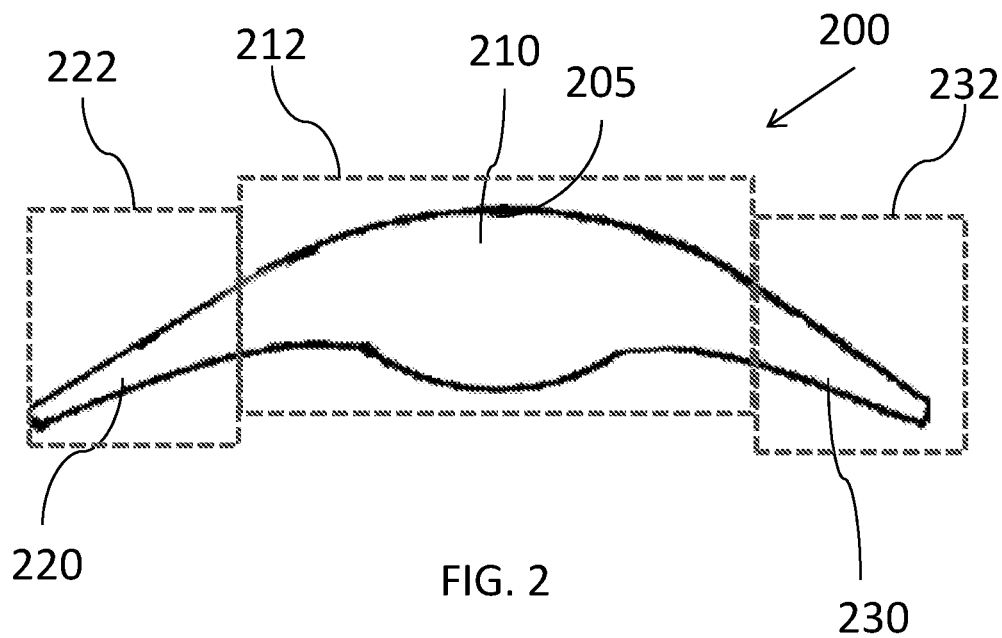
FIG. 2 is another side view of a palatal element of a removable oral device, in accordance with certain examples.

In certain examples and referring to FIG. 2, a palatal element 200 is shown that comprises areas 210, 220 and 230. Area 210 is designed to provide a desired thickness to reduce the overall oral volume and comprises an apex 205, which is typically the highest point of the palatal element 200. Areas 220 and 230 are designed to be positioned adjacent to certain teeth and assist in retention of the removable oral device in place. In certain configurations, the material present in area 210 (as shown by box 212) may be harder than the materials present in areas 220, 230 (as shown by boxes 222 and 232). The softness of the materials at areas 220, 230 can be the same or can be different. For example, different materials can be used at the areas 220, 230 in the production methods than the material used at area 210. In other instances, post-production techniques, e.g., cross-linking, hardening, etc. may be implemented to increase the hardness at the area 210 as compared to a hardness at an area 220, 230. In some examples, areas 220, 230 comprise softer materials to permit these areas to function, at least to some degree, as a seal or gasket that prevents foods or other materials from entering into any space between a palatal surface of the palatal element and the roof of the user's mouth. Depending on the particular materials used, the hardness at the areas 220, 230 is at least 2×, 3×, 4× or 5× less than the hardness at area 210. The hardness at area 210 is generally less than that of glass or hard plastics such that the area 210 can flex to some degree during chewing of food.

Referring again to FIG. 1, the hardness of the materials may decrease from a central area C1 toward the edges E1, E2. In some examples, hardness may gradually decrease from C1 to E1, E2, whereas in other instances an interface can be present between various portions of the palatal element where the softer materials meet the harder materials. In some embodiments and referring again to FIG. 2, the material present in area 210 (as shown by box 212) may be harder, e.g., may have a higher Vickers Hardness value (HV), than the materials present in at least some areas within areas 220, 230 (as shown by boxes 222 and 232). While the exact methodology used to determine a HV value can vary, suitable methods typically involve indenting the test material with a diamond indenter under a selected load, e.g., 30 kgf of force (kgf), and measuring the depth of the indentation. The indentation depth can be correlated to materials hardness using suitable lookup tables or calibration curves. Commercial instruments to determine Vickers hardness values are available from Shimadzu (Japan) and LECO (Japan). In some instances, the protocols described in ASTM E384—16 entitled "Standard Test Method for Microindentation Hardness of Materials" can be followed to determine Vickers hardness values. The hardness/softness of the materials at areas 220, 230 can be the same or can be different. In some examples, areas 220, 230 comprise softer materials (compared to the hardness of the material at area 210) to permit these areas to function, at least to some degree, as a seal or gasket that prevents, foods or other materials from entering into any space between a palatal surface of the palatal element and the roof of the user's mouth. Depending on the particular materials used, the hardness at the areas 220, 230 can be at least 2×, 3×, 4× or 5× less than the hardness at area 310. For example, the Vickers hardness value (HV) at areas 220, 230 can be at least 5% less, at least 10% less, at least 20% less, at least 30% less, at least 40% less or at least 50% less than the HV value at the area 210. The hardness at area 210 is generally less than that of glass or hard plastics such that the area 210 can flex to some degree during chewing of food. For example, in some instances, the HV at the apex 205 may be 20 HV or more, whereas the HV at each of the edges 220, 230 can independently be less than 20 HV. In other examples, the HV value at the apex 205 can be 10 HV or more and the value at the edges 220, 230 can be less than 10 HV. In other configurations, the HV at the apex 205 can be 10 HV or more and the value at the edges 220, 230 can be less than or equal to 5 HV. The exact level of hardness used may vary from subject to subject. For example, certain individuals may find hard apex areas to be uncomfortable, and the material hardness at the apex can be lowered for those subjects by, for example, reducing the level of cross-linking in the polymeric materials used to produce the palatal element 200.

In some embodiments, the material used at the edges may be the same or may be different than material present at the apex of the palatal element and different techniques can be used to couple the material at the edges to material at the apex. For example, the material at the edges can be the same material but it may be cross-linked to a lesser degree to be softer than the material at the apex section of the palatal element. In other examples, a different material is used for the edges and is coupled to other material of the palatal element through one or more cross-linkers. For example, a central portion or apex portion of the palatal element may first be built up, e.g., using printing, sprinkle-and-pour techniques or other techniques, and then the edges can be placed adjacent to the central portion and couple to the central portion through one or more chemical bonds. The edges typically integrate with the central portion without the need to use an adhesive or other material to retain the edges to the central portion. Where two different materials are used, there is generally no discernible interface between the materials which might be obtrusive or uncomfortable. For example, layers of the apex material can be built up using a first material, and a second material can then be coupled to the first material to provide the edges of the palatal element.

In some embodiments, the material present in the palatal element may be an acrylic, a polycarbonate, a polyolefin, a thermoplastic polymer, a thermoset polymer or combinations thereof. If desired, the material may comprise elastomers, elastomeric fibers or other materials to alter the overall hardness of one or more areas of the palatal element. The materials can be cross-linked or cured by sprinkling or mixing a cross-linker with the material either pre-use or post-use. For example, a mold of the user's mouth can be used with the material to provide a palatal element. The material can be added to the mold (in one or more desired areas) and then cross-linked by sprinkling a cross-linker onto the added material in the mold. In some examples, the palatal surface and/or tongue surface can be smooth to prevent food from sticking to the removable oral device. If desired, however, the surface may be bumpy or comprise ridges or other features to mimic the tongue feel when the tongue is placed against the roof of the user's mouth. In other instances, the palatal element may comprise one or more coatings including, but not limited to, anti-bacterial coatings, non-stick coatings or coatings which may impart color or ornamental designs to the palatal element. In some embodiments, each area of the palatal element may comprise an acrylic material including polyacrylates, methacrylates and the like. In some embodiments, one or more areas of the may comprise Silident materials, clays, alginates, or other materials which can generally retain their shape during eating forces.

In some examples, the material at the edges of the palatal element may be thermally sensitive and can soften to an even greater degree at mouth temperatures than when the palatal element is outside of the mouth. For example, the Vickers Hardness of the material at the edges can be selected to decrease when the removable oral device is inserted into the mouth and reaches the temperature of the mouth compared to the Vickers hardness of the edges when the palatal element is at room temperature. In some embodiments, the Vickers hardness of the material of the edges decreases at least 5%, at least 10% or at least 20% at about 37 degrees Celsius compared to the Vickers hardness at room temperature (about 25 degrees Celsius).

Figure 3:
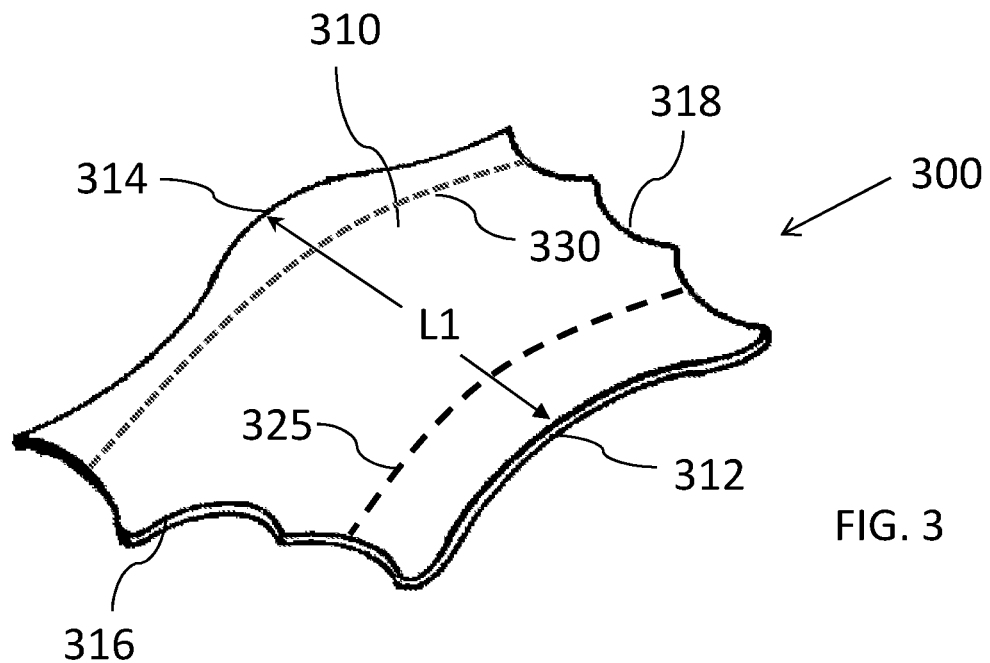
FIG. 3 is a perspective view of a palatal element of a removable oral device, in accordance with certain configurations.

In certain examples, a perspective view of a palatal element is shown in FIG. 3. The palatal element 300 comprises a body 310 with sides 312, 314, 316 and 318. Side 312, e.g., an anterior side, generally is adjacent and/or contact inner surfaces of the anterior teeth. Side 314, e.g., a posterior side, is positioned in the back of the mouth when the removable oral device is inserted. Side 316 can be positioned adjacent to the inner surfaces of tooth numbers 1-4 (or 2-4 when the wisdom teeth have been removed) when the removable oral device is inserted. Side 318 can be positioned adjacent to the inner surfaces of tooth numbers 13-16 (or 13-15 when the wisdom teeth have been removed) when the removable oral device is inserted. The length L1 of the body 310 may vary and is generally designed to be large enough so the body 310 provides a desired oral volume reduction but is not so large that a user may gag or have difficulty breathing when the removable oral device is inserted. As noted herein, the sides 316, 318 may comprise a softer material than material present at an apex of the palatal element 300, e.g., the Vickers hardness at the edges 316, 318 may be at least 2×, 3×, 4× or 5× less than the hardness at an apex area. For example, the Vickers hardness value (HV) at the edges 316, 318 can be at least 5% less, at least 10% less, at least 20% less, at least 30% less, at least 40% less or at least 50% less than the HV at the apex area of the palatal element 300.

In some examples, some portion or the anterior side and/or posterior side can be removed to facilitate a better user experience with the removable oral device. For example, a volume of the palatal element toward the anterior side 312, e.g., the volume from the line 325 forward toward the anterior side 312 can be removed or reduced, e.g., by trimming, sanding, cutting, etching, etc., to reduce lisping. In certain embodiments, about 1-10% of the volume from the anterior side 312 can be removed to assist in reduction of lisping when the removable oral device is in place. If desired, a crescent shape (or other shape) may be provided at the anterior side 312 to reduce lisping. In some examples, trimming the posterior side 318 of the device in a crescent shape can be performed to eliminate or reduce contact with the soft palate to address individuals with heightened gag reflex. For example, a posterior volume from line 330 toward the posterior side 314 can be removed to reduce the likelihood of gagging when the removable oral device is present in the mouth. In some examples, a crescent shape (see FIG. 5) or other non-linear shape may be provided at the posterior side to reduce gagging. In other instances, the palatal element can be trimmed or cut into various shapes for purely ornamental reasons that might increase the overall aesthetic appearance of the palatal element but generally does not provide any particular function. In certain embodiments, about 1-15% of the volume from the posterior side 314 can be removed to assist in reducing the likelihood of gagging. A palatal element can then be trimmed or shaped as desired to provide a desired overall volume reduction while at the same time minimizing or reducing the likelihood of lisping and/or gagging. In addition, the palatal element can be trimmed or shaped to provide a more aesthetically pleasing palatal element rather than one which imparts any particular anti-lisping function or other function.

Figure 4:
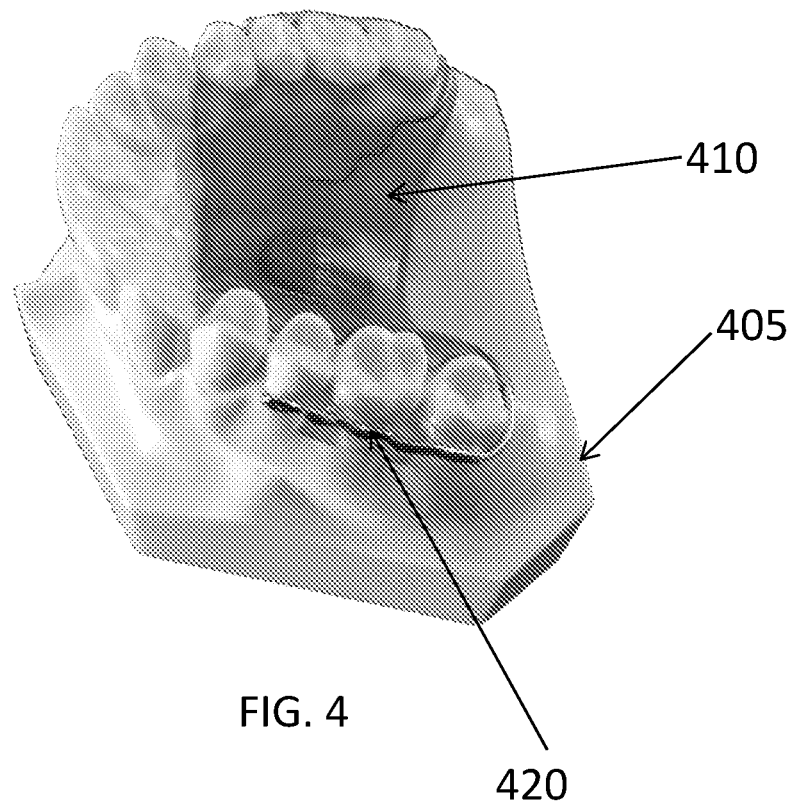
FIG. 4 is a perspective view of a removable oral device positioned within a tooth mold, in accordance with certain examples.

In certain configurations, the removable oral devices described herein may also comprise a clasping element. As noted herein, the clasping element is optional but may be present to assist removal of the palatal element from the user's mouth. Referring to FIG. 4, a perspective view of a removable oral device 400 comprising a palatal element 410 and a clasping element 420 is shown positioned around a tooth mold 405. The clasping element 420 is generally configured with a support element or wire that is embedded within a material such that the wire itself does not directly contact the outer surfaces of the teeth. While the clasping element may be configured as a wire or wires in some instances, in other cases the clasping element may comprise a plastic or flexible moldable material etc., or other non-metal based materials. In some examples, the clasping element may comprise chromium-nickel alloys such as, for example, Elgiloy materials which are cobalt-chromium-nickel alloys. In other examples, the clasping element may comprise titanium, titanium alloys, nickel titanium materials such as Nitinol, etc. In some embodiments, the material of the clasping element is generally inert so that it does not tarnish, rust, corrode or otherwise degrade during use of the removable oral device. In certain configurations, some portion of the wire may directly contact the rear surface of the back teeth to assist in retention of the palatal element 410 against the roof of a user's mouth.

Figure 5:
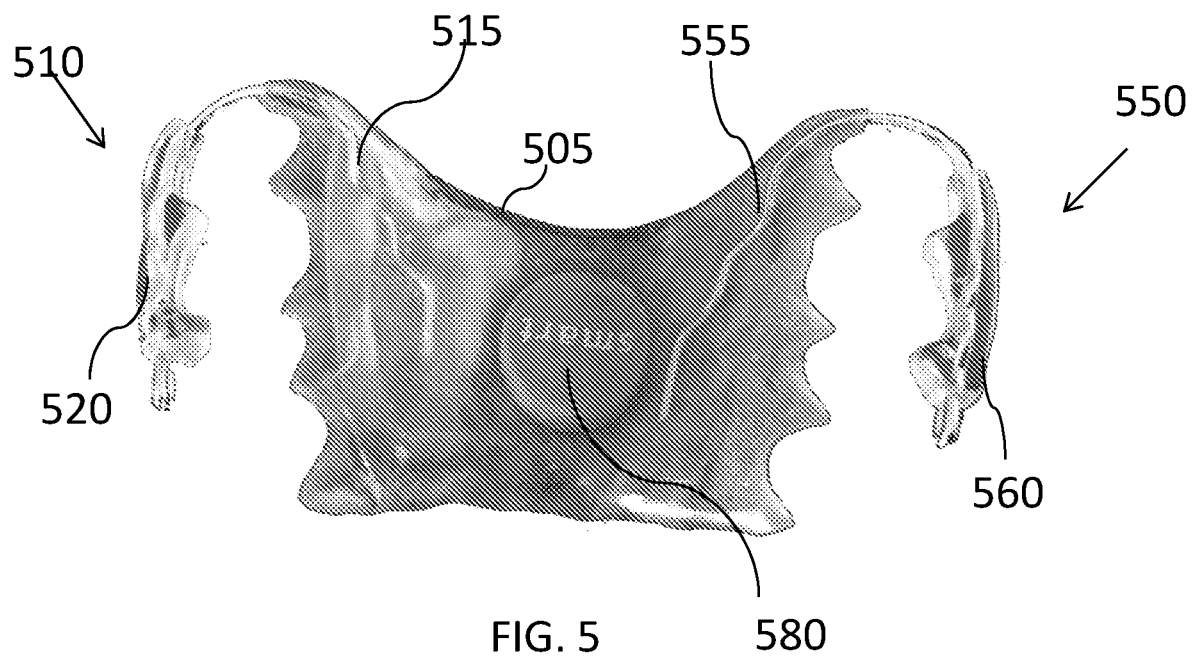
FIG. 5 is a bottom view of a removable oral device comprising a palatal element and clasping elements, in accordance with some examples.

In certain configurations, the wire of the clasping element may be a continuous wire which runs from one side of the palatal element 410 to the other or two or more separate wires can be present with one wire being present in a respective clasping element. For example and referring to FIG. 5, a clasping element 510 comprises a wire 515 and associated material 520 on some portion of the wire. Another clasping element 550 comprises a wire 555 and associated material 560 on some portion of the wire 555. Some portion of the wires 515, 555 is also embedded within a body of a palatal element 505. The material 520, 560 generally rests against outer surfaces of the teeth when the palatal element 505 is engaged to the roof of the mouth. The wires 515, 555 can assist in removal of the removable oral device from the mouth and/or assist in retaining the removable oral device in place. For example, surface tension between a palatal surface of the palatal element 505 and the roof of a user's mouth can "lock" the palatal element 505 to the roof of the mouth. The wires 515, 555 can provide leverage to assist in breaking of the surface tension and removal of the removable oral device from the mouth. An optional sensor 580 is also shown as being embedded in the palatal element 505. Illustrative sensors are described, for example, in the commonly assigned patent applications incorporated herein by reference. While two clasping elements 510, 550 are shown in FIG. 5, only a single clasping element may be present if desired or no clasping elements may be present at all.

In certain configurations, the palatal element and/or clasping element(s) of the removable oral devices are designed to not permanently retain the removable oral device in a user's mouth. In particular, the palatal element may lock or be held in place to the roof of the mouth without the user of any fasteners. In other examples, the clasping element can be configured to provide a friction fit against the outer surfaces of the back teeth, e.g., the clasping element is designed to contact the outer surfaces of tooth numbers 1-4 or 2-4 and/or tooth numbers 13-16 or 13-15. In some instances, the clasping element may comprise one or more portions which are positioned between two or more of tooth numbers 2-4 and/or tooth numbers 14-16 to assist in anchoring of the palatal element to the roof of the user's mouth. The removable oral device generally is designed to lack any wires, supporting element or anchoring elements which extend around, through or near tooth numbers 5-12 such that the clasping element does not alter the position of the teeth in use. As noted herein, the clasping element is also generally not designed to retain the teeth in any particular position. In some configurations, the removable oral device does not include any clasping element, supporting element, wire, etc. that engage the anterior teeth, e.g., outer surfaces of tooth numbers 5-12 or 4-11 do not contact the clasping element.

In certain embodiments, a removable oral device comprises a palatal element coupled to a clasping element. As noted herein, the palatal element is configured to contact a roof of a user's mouth at a palatal surface and can be configured to lower a vaulted area of the roof of the mouth to decrease an overall oral volume of the mouth to a first oral volume. The body of the palatal element may comprise a variable hardness across a tongue surface of the body. In some examples, the clasping element is configured to assist in removal of the removable oral device when the removable oral device is inserted into the user's mouth. In certain configurations, the tongue surface of the palatal element is compressible at an edge of the palatal element adjacent to the clasping element and is substantially non-compressible at an area adjacent to the roof of the user's mouth. For example, surfaces adjacent to the side edges, anterior edges and/or posterior edges may be soft and compressed with force from the tongue, whereas surfaces in-line with the apex surface may be substantially non-compressible by force from the tongue. It may be desirable to select materials for the edges that have a Vickers hardness soft enough to permit tongue forces to compress the material. In addition, various techniques can be used in the production process to provide areas with a different Vickers hardness. It may also be desirable to select materials for an apex or central portion of the palatal element to have a Vickers hardness high enough such that substantially no compression of the apex or central portion occurs under tongue force or tongue pressure.

In some embodiments, the palatal element may comprise a temperature sensitive thermally expandable material configured to increase its overall volume at a body temperature of the user. For example, certain hydrogels or other gel or sol based materials may thermally expand with increasing temperature, which can act to increase the overall volume occupied by the palatal element. This configuration can result in less of a reduction in oral volume when the removable oral device is initially inserted and an increased reduction in oral volume during continued use of the removable oral device. In some examples, the thermally expandable material can be selected so that its overall volume increases by at least 5%, at least 10%, at least 15% or at least 20% when the palatal element temperature increases from around room temperature, e.g., about 25 degrees Celsius, to around body temperature, e.g., about 37 degrees Celsius. The thermally expandable material may be present, for example, in an internal bladder or compartment present in the palatal element and may or may not be accessible by the tongue during use of the removable oral device. Illustrative thermally expandable materials include, but are not limited to, thermally expandable methyacrylates, thermally expandable epoxy materials, thermally expandable hydrogels, thermally expandable aerogels and other similar materials.

Figure 6:
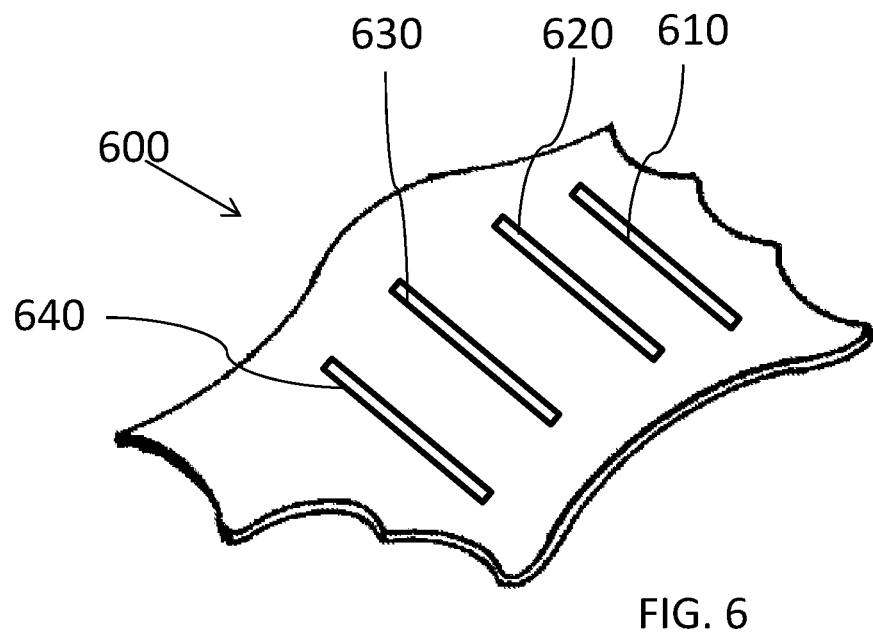
FIG. 6 is an illustration of a palatal element with grooves, in accordance with certain examples.

In certain examples, the palatal element may comprise one or more grooves, holes or other features present on a tongue surface or a palatal surface as desired. For example and referring to FIG. 6, a palatal element 600 may comprise one or more grooves such as grooves 610, 620, 630 and 640. The exact number of grooves can vary from one to about ten, for example. The grooves can assist in breaking any seal between the palatal surface and the roof of a user's mouth and/or can decrease the overall weight of the device. If desired, the grooves can be replaced with holes or other features. The grooves, holes, etc. generally do not penetrate into or through the tongue surface of the palatal element 600 to avoid materials such as food from becoming trapped in the palatal element 600. As noted herein, where grooves or other features are present, one or more sides of the palatal element 600 may also comprise soft surfaces or the palatal element may comprise a body with variable hardness. To provide the grooves or other features, a suitable mold that comprises features to impart grooves can be used. In other instances, post-production techniques can be implemented to provide the grooves or other features in one or more surfaces of the palatal element.

In certain configurations, the removable oral device may be modular to permit a user to assemble two or more palatal elements to each other. Referring to FIGS. 7A and 7B, two palatal elements 710, 720 are shown. A palatal surface of the element 720 may snap into or engage a tongue surface of the element 710 to retain the palatal elements 710, 720 to each other for some period. In certain configurations, the palatal element 720 may comprise projections or bosses 722, 724 which can engage corresponding holes or apertures (not shown) in an under surface of the palatal element 710 to retain the element 720 to the element 710. Coupling of the element 720 to the element 710 reduces the overall oral volume to a second oral volume which is less than that provided by either of the elements 710, 720 alone. One of the palatal elements 710, 720 may comprise one or more clasping elements as described herein to assist in retention of the assembly to the roof of the mouth of a user. If desired, a third palatal element, fourth palatal element, etc. can be coupled to further reduce the oral volume. Modular palatal elements may be particularly desirable for initial weight loss and downstream weight management. For example, both palatal elements 710, 720 can initially be used to provide a greater volume reduction and assist in weight loss from reduced caloric intake. Once the user reaches their weight goal or their BMI or body fat drops below a desired level, then one of the palatal elements 710, 720 can be removed to assist the user in maintaining their current weight using only the single palatal element during ingestion of food. In the alternative, the use of multiple combined palatal elements can force a user to ingest a particular quantity of food over a desired period. For example, where a user eats food too quickly even with the removable oral device inserted, a second palatal element can be coupled to the first palatal element to provide a further reduction in oral volume to increase the overall eating time for the same quantity of food.

In some instances, the removable oral devices described herein can be produced by printing, e.g., three-dimensionally printing, a removable oral device using a first material. For example, a removable oral device comprising a palatal element can be three-dimensionally printed using a three dimensional printer and suitable materials which can be printed and can provide desired physical properties, e.g., biocompatible inks/materials or other suitable materials can be used. The template for the palatal element can be obtained using numerous methods (as noted below) and used by a system comprising the three dimensional printer to print the palatal element. The three-dimensional printer typically includes one or more print heads and a stage or support that can receive material from the print heads to form the printed palatal element. Successive layers are built upon the support to provide the printed palatal element. The resulting printed palatal element can be shaped or modified to provide a desired final shape or size if desired. For example, some portion of the anterior or posterior sides of the printed palatal element can be removed. In some examples, some portion of an anterior side, e.g., a side toward the front teeth, can be removed to reduce lisping. In other examples, some portion of a posterior side, e.g., a side toward the back of the throat, can be removed to avoid or deter gagging. If desired, however, these portions of the palatal element can be omitted during the printing process to avoid post-printing shaping or trimming steps.

In certain examples, the exact nature and type of three-dimensional printing used to produce the components of the removable oral device may vary. Illustrative three-dimensional printing technologies include, but are not limited to, selective laser sintering (SLS), fused deposition molding (FDM), laminate object manufacturing (LOM), rapid prototyping, and three-dimensional inkjet printing. Three-dimensional printing methods using digital light processing (DLP) or an injection through a series of tiny nozzles or a single nozzle may use photo-curable materials which can be cured by UV/Visible light. These two methods are rapid, low cost, high resolution, and easy to use. Three-dimensional removable oral devices can be produced using ink-jet printing techniques that can use several different materials, e.g., from different reservoirs or cartridge, to provide a photo-curable liquid compositions which can be cured by exposure to UV/Visible light. The photo-curable "ink" in the ink-jet printing process is provided through one or more nozzles on a support stage with a pattern defined by a computer aided design (CAD) file or other three-dimensional coordinates. In one exemplary illustration, successive layers of the palatal element can be "built up" by placing individual layers on the printer support and curing, at least to some degree, the printed layer prior to addition of successive layers. Layers can be added in individual areas until a desired final shape is reached. In some instances, a material with a different hardness can be printed at the edges of the palatal element to provide softer edges. In alternative configurations, the material at the edges may comprise the same basic material as present at the apex portion of the palatal element, but a different cross-linker, or lower amounts of the same cross-linker, can be disposed at the edges to provide the softer edges.

In some embodiments, the final three-dimensionally printed removable oral device can then be washed or treated with one or more other materials if desired, e.g., one or more coatings or other materials can be applied to the printed palatal element, clasping element or both. In one three-dimensional printing technique using digital light processing, the photo-curable liquid can be placed in a reservoir. Exposure of certain areas to the curing light can provide layers which can be used to build up the removable oral device to a desired thickness. Once a layer has been cured by UV/Visible light, a building platform moves in the z-direction depending on the thickness of the layer. This process is repeated until all layers are formed and/or a desired shape is formed. Illustrative three-dimensional printers include, but are not limited to, those commercially available from Objet or Master, those supplied by Carima and The Form 1 supplied by Formlabs.

In some examples, the materials used by the three-dimensional printer may be photo-curable, heat curable, UV curable or cured by adding one or more external curing agents to the printed palatal element to harden the materials (at least to some degree). The exact materials used include, but are not limited to, acrylates, methacrylates, acrylic polymers and co-polymers, functionalized bisphenol A methacrylates such as a monofunctional bisphenol A dimethacrylate or a difunctional bisphenol A dimethacrylate, a diglycidyl methacrylate ester of bisphenol-A or a bisphenol-A diglycidyl ether and other materials. In some examples, the printed palatal element of the removable oral device may comprise one or more of ethylene glycol dimethacrylate, diethylene glycol dimethacrylate, triethylene glycol dimethacrylate, polyethylene glycol dimethacrylate, 2,2 bis[4-(methacryloxy ethoxy)phenyl]propane, tricyclodecane dimethanol dimethacrylate, 1,10-decanediol dimethacrylate, 1,6-hexanediol dimethacrylate, 1,9-nonanediol dimethacrylate, neopentyl glycol dimethacrylate, 2-hydroxy 1-3 dimethacryloxy propane, trimethylolpropane trimethacrylate, ethoxylated trimethylol propane trimethacrylate, ditrimethylolpropane tetramethacrylate, tris (2-hydroxy ethyl)isocyanurate trimethacrylate, dipentaerythritol pentamethacrylate, ethoxylated pentaerythritol tetramethacrylate, propoxylated glyceryl trimethacrylate, propoxylated trimethylolpropane trimethacrylate, and a polyester dendrimer. The exact material used, or combinations of the materials used, can be selected to provide a palatal element which provides sufficient hardness to permit chewing but is not so hard as to be uncomfortable in the mouth. For example, the material can be cured to provide a feel similar to the native roof of the mouth. If desired, the printed palatal element may comprise grooves, bumps or other features present on a tongue surface as described the SCIINTAK-700100 application. Such features may be provided during the printing process or added post-printing.

In certain examples, the clasping element of the removable oral device may also be printed or the palatal element can be printed with the clasping element or elements present on the printer support. For example, a clasping element in the form of a metal wire (or a support material other than metals) can be present on the printer stage, and the palatal element can be printed onto the clasping element to provide the removable oral device with an embedded wire as a clasping element or where a portion of the wire of the clasping element is embedded within the palatal element.

In some examples, the printed palatal element can be heat cured by placing it in an oven to harden the body of the palatal element. If desired, heat tape, shielding tape or other materials can be placed at the edges of the palatal element to prevent hardening of these areas to the same degree as an apex portion of the body. In other examples, one or more curing agents can be deposited onto the entire body of the palatal element or just at apex areas to provide softer edges when the palatal element is cured.

In certain examples, one or more photo-curing agents can be added to the printed palatal element (or clasping element or both) or may be present in the "ink" used to print the palatal element. For example, the polymeric material of the palatal element can be mixed with a photo-curing agent and the mixture is deposited in additive layers to form the palatal element. Illustrative photo-curing agents include, but are not limited to, acetophenone, anisoin, anthraquinone, (benzene) tricarbonylchromium, benzil, benzoin, benzoin ethyl ether, benzoin isobutyl either, benzoin methyl ether, benzophenone, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, 4,4'-bis(dimethylamino)benzophenone, camphorquinone, 2-chlorothioxanthen-9-one, (cumene) cyclopentadienyliron(II)hexafluorophosphate, dibenzosuberenone, 2,2-diethoxyacetophenone, 4,4'-dihydroxybenzophenone, 2,2-dimethoxy-2-phenylacetophenone, 4-(dimethylamino)benzophenone, 4,4'-dimethylbenzyl, 2,5-dimethylbenzophenone, 3,4-dimethylbenzophenone, 4'-ethoxyacetophenone, 2-ethylanthraquinone, ferrocene, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-methylbenzophenone, 3-methylbenzophenone, methylbenzoylformate, 2-methyl-4'-(methylthio)-2-morpholinopropio-phenone, phenanthrenequinone, 4'-phenoxyacetophenone, thioxanthen-9-one, triacrylsulfonium hexafluoroantimonate salts, triarylsulfonium hexafluorophosphate salts, 4,6-trimethylbenzoyldiphenylphosphine oxide, 2,6-dimethyoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-prophylphenylphosphine oxide, bis-(2,6-dichlorobenzoyl)-1-naphthylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzo yl)-2,4,4-trimethylpentylphosphine oxide and those compounds commercially available from Dow Chemical Company as UVI 6950, UVI 6970, UVI 6974, UVI 6976, and UVI 6990.

In certain examples, the printed palatal element (or the clasping element or both) may comprise fillers, particles, powders, reinforcing materials, etc. to impart overall desired physical properties to the removable oral device. For example, silica based powders, fillers, fibers, etc. can be added to the removable oral device. In other instances, carbon fibers or particles can be added to the palatal element to alter its overall strength and/or weight. Pigments, colorants, dyes, texturizing agents, UV stabilizers, or other materials may also be present. If desired, suitable ornamental features, logos, etc. may also be printed or otherwise provided on the palatal element, clasping element or both.

In some examples, two different materials can be used to print the removable oral device. For example and referring to FIG. 8, a first material can be used to print the body at or adjacent to an apex surface 810, e.g., a surface adjacent to the palate and opposite a tongue surface of the palatal element, and a second material can be used to print the body at the edges 812, 814. It may be desirable, for example, to print the edges 812, 814 using a softer material to increase the overall comfort of the removable oral device in the mouth and/or reduce lisping. If desired, some portion of the clasping elements 820, 830 can also be printed. For example, material can be printed onto the wire support of the clasping elements 820, 830. The exact shape of the front edge 815 and the back edge (not shown) may vary as noted below.

In some examples, one or more sensors can be disposed on the printer support prior to printing or during printing to embed the sensor with the printed palatal element. Such sensors can be disposed in an automated manner or manually during the printing process. Other devices such as bladders, electrodes, etc. can also be added to the palatal element, the clasping element or both as the device is being printed. Where sensors (or other electrical components) are present, the printing process and/or curing conditions may desirably be performed at temperatures and conditions where damage to the sensors (or other electrical components) does not occur. If desired, shielding tape, heat tape, etc. may be disposed over areas comprising the sensors (or other electrical components) to prevent damage by exposure to heat and/or UV/Visible radiation. Illustrative sensors include, but are not limited to, a camera, an electrode, a bar code reader, a processor, an optical transmitter, an optical receiver, a RFID tag, a piezoelectric sensor, an accelerometer, a chewing sensor, etc. Additional sensors and electrical components can also be included in the palatal element as desired.

In some examples, three-dimensional printing techniques can be used to print a molding plate which the user can insert into their mouth to provide a mold of their mouth. For example and as noted in more detail below, the printed molded plate can be tailored or customized for the user and used in combination with an impression material, e.g., an alginate or other materials, to provide a mold of the upper mouth of the user.

In another configuration of producing a removable oral device comprising a palatal element and a clasping element, a method comprises imaging an oral cavity of a human. The imaged oral cavity can then be used to provide a removable oral device from the imaged oral cavity. The imaging of the oral cavity can be performed internally or externally as desired. The produced removable oral device comprises a palatal element coupled to a clasping element, in which the palatal element is configured to contact a roof of a user's mouth at a palatal surface. The clasping element, when present, is configured to assist in removal of the palatal element from the mouth and/or to retain the palatal surface of the palatal element against the roof of the user's mouth when the removable oral device is inserted into the user's mouth.

Various different methods and systems can be used to image the oral cavity of the mouth. In some examples, a user may insert a probe or device into their mouth to permit scanning of the surfaces, including the palatal surfaces, to provide a two-dimensional or three-dimensional representation of the user's mouth. For example, a camera head can be inserted into the mouth and used to capture video or still images of the mouth surfaces. The camera images may be used to digitally reconstruct a representation of the oral cavity, which can be used to provide the removable oral device, e.g., can be used to print the removable oral device. For example and referring to FIG. 9, a system which comprises a probe 910 can be electrically coupled to a processor 920, e.g., in a wired or wireless manner, which is used to provide a three-dimensional image from the measurements of the probe 910. As noted in more detail in the commonly assigned U.S. 62/477,766 incorporated herein by reference, the combination of oral scanning and three-dimensional printing can permit real-time production of a removable oral device for a user, e.g., in a health care provider's office or at a point of sale kiosk. If desired, imaging can instead be performed in an external manner by placing a probe adjacent to outer surfaces of the cheeks and imaging from the outside of the user's mouth.

In certain configurations, the exact nature of the probe 910 can vary. In some examples, the probe 910 comprises an ultrasound scanner head which can be used to obtain detailed images of the oral cavity. These detailed images can be used to provide three-dimensional coordinates which are used to provide the removable oral device. In other instances, the probe 910 may comprise a camera or image head such as a video camera, charge-coupled device, photodiode camera or other suitable cameras which can capture still or moving images from the oral cavity. The captured images can be used to provide three-dimensional coordinates which are used to provide or produce the removable oral device. In some examples, the probe 910 is configured to only measure the upper surfaces of the oral cavity including the palatal surfaces. Various different types of imaging can be used including, but not limited to, panoramic imaging, X-rays, CT scanning, magnetic resonance imaging, ultrasound imaging, infrared imaging, etc. While not required, the imaging desirably is one which uses lower energy imaging, e.g., no X-rays, to avoid undue exposure to potential ionizing radiation.

In certain configurations, the production methods described herein can use the image to produce the removable oral device with areas of the body adjacent to the clasping element being softer than other areas of the body. In other configurations, the method comprises imaging the oral cavity using an image head electrically coupled to a wireless device. For example, the probe can wirelessly transmit images or coordinates to a mobile device such as a phone, laptop or tablet to permit a user to obtain and take the coordinates and use them to print or otherwise produce a removable oral device at a later time. In some embodiments, the wireless images can be provided to a pharmacy which can produce the removable oral device using three-dimensional printing or other techniques. Use of the removable oral device for weight management can be subject to federal regulation and may require a prescription from a physician. The probe can permit a user to image their oral cavity and then transfer that information to the pharmacy which can fill the prescription by producing the removable oral device or ordering it from a third party authorized to fill prescriptions.

In some examples, a user may interact with a kiosk or system which images their oral cavity and provides three-dimensional coordinates based, in part, on user information such as height, weight, etc. As described in more detail in U.S. 62/477,766, the user can stand on a platform or scale and enter their height into the system. The user may then insert the probe into their mouth (or hold it adjacent to their mouth) to scan their mouth and provide three-dimensional coordinates from the mouth scan. Based on the user's information, the system can select an overall thickness for the removable oral device. For example, where the user is 5-10 pounds over their target weight, e.g., 5-10 pounds above a body mass index of 25, the system may use the image to provide a removable oral device with suitable dimensions to reduce the oral volume by about 15% when the device is in place. Where the user is 10-20 pounds over their target weight, e.g., 10-20 pounds above a body mass index of 25, the system may use the image to provide a removable oral device with suitable dimensions to reduce the oral volume by about 20% when the device is in place. Where the user is 20-30 pounds over their target weight, e.g., 20-30 pounds above a body mass index of 25, the system may use the image to provide a removable oral device with suitable dimensions to reduce the oral volume by about 25% when the device is in place. Where the user is considered obese or morbidly obese, the system may use the image to provide a removable oral device with suitable dimensions to reduce the oral volume by about 30-35% when the device is in place. As the user loses weight using the device, they can return and obtain an updated removable oral device which has a lower thickness if desired. In this manner, the system can tailor or customize the removable oral device based on oral images and based on a user's physical characteristics and/or desired weight management goals. In some examples, the system may use bioelectrical impedance to measure the user's body fat percentage, and based on the measured body fat percentage, select a thickness for the removable oral device. This thickness can be different with higher palatal element thicknesses typically desired where higher body fat percentages are identified, e.g., for body fat percentages above 25% in men and 32% in women, a thickness which reduces the overall oral volume by about one-third can be used.

In some examples, the probe used to capture the images may plug into or interface with a phone, mobile device, tablet, wearable device or other device to permit the user to obtain the images of their oral cavity at home. The obtained oral images can then be transmitted to a third party to produce the removable oral device. If desired, physical parameters of the user, e.g., height, weight, gender, age, etc. can also be considered during production of the removable oral device. The probe may plug into a USB port, a micro-USB port, Lightning port, an Ethernet port, etc. of the mobile device or may wirelessly transmit images to the mobile device or other electronic device.

In another configuration, a method of using a removable oral device comprises imaging an oral cavity of a human using an image head configured to receive a disposable cover, and printing a removable oral device from the imaged oral cavity using a first material. The printed removable oral device comprises a palatal element coupled to an optional clasping element, in which the palatal element is configured to contact a roof of a user's mouth at a palatal surface, and wherein the palatal element comprising a body comprising a thickness configured to lower a vaulted area of the roof of the mouth to decrease an overall oral volume of the mouth to a first oral volume. The clasping element, when present, can be configured to assist in removal of the removable oral device from the mouth and/or to retain the palatal surface of the palatal element against the roof of the user's mouth when the removable oral device is inserted into the user's mouth.

In certain configurations, the method comprises printing areas of the body adjacent to the clasping element using the imaged oral cavity and a second material softer than the first material. In other instances, the method comprises printing a second removable oral device from the imaged oral cavity, wherein the second removable oral device comprises a second palatal element comprising a second body comprising a thickness configured to lower a vaulted area of the roof of the mouth to decrease an overall oral volume of the mouth to a second oral volume less than the first oral volume. As noted in more detail herein, one or more sensors, electrodes or other devices can be embedded in the removable oral device during the printing process. The removable cover is configured to engage an image head through a friction fit and permits many different users to use the same image head without the need to sanitize or clean the image head between users. In some examples, the cover is transparent to the particular methods used to image the oral cavity, e.g., does not absorb or deflect ultrasound waves, light, etc. If desired, the cover may comprise a thickness and/or shape which mimics that of the palatal element of the removable oral device so the image head can be used to assess the quality of the fit of a potential removable oral device prior to printing. In some examples, the cover may be elastomeric or compressible to assist in obtaining a desired palatal shape for production of the palatal element. Adjustments can be made based on the feedback before the removable oral device is printed. In some examples, the method comprises three-dimensionally printing the palatal element using a photo-curable material. In other examples, the method comprises disposing one or more wires on a printer support as the clasping element and printing the photo-curable material into the printer support comprising the one or more wires to provide the removable oral device. In some examples, the method comprises photo-curing the printed palatal element using UV/Visible light. In certain embodiments, the method comprises printing each of the palatal element and the clasping element using a photo-curable material. In some instances, the method comprises three-dimensionally printing the removable oral device using an inkjet three-dimensional printer. In certain examples, the method comprises three-dimensionally printing the removable oral device using digital light processing.

In another configuration, a method may comprise imaging an oral cavity of a human, printing a mold from the imaged oral cavity, and using the printed mold to provide a removable oral device comprising a palatal element coupled to a clasping element. The palatal element is configured to contact a roof of a user's mouth at a palatal surface, the palatal element comprising a body comprising a thickness configured to lower a vaulted area of the roof of the mouth to decrease an overall oral volume of the mouth to a first oral volume. The clasping element is configured to assist in removal of the removable oral device from the mouth and/or to retain the palatal surface of the palatal element against the roof of the user's mouth when the removable oral device is inserted into the user's mouth.

In some configurations, the method comprises using an image head configured to receive a disposable cover to image the oral cavity. In other examples, the method comprises injecting a material into the printed mold to provide the removable oral device. The injected material may be, for example, any of those materials described in connection with three-dimensional printing or other materials commonly used in injection molding processes. In some examples, the method comprises disposing material into the mold and extruding material from the mold to provide the removable oral device. In certain examples, the method comprises placing a gasket in the mold prior to providing the removable oral device, wherein the gasket is present between the body of the palatal element and the clasping element. In some examples, the method comprises three-dimensionally printing the palatal element using a photo-curable material. In other embodiments, the method comprises disposing one or more wires on a printer support as the clasping element and printing the photo-curable material into the printer support comprising the one or more wires to provide the removable oral device. In some examples, the method comprises photo-curing the printed palatal element using UV/Visible light. In further examples, the method comprises printing each of the palatal element and the clasping element using a photo-curable material. In some instances, the method comprises three-dimensionally printing the removable oral device using an inkjet three-dimensional printer. In other embodiments, the method comprises three-dimensionally printing the removable oral device using digital light processing.

Figure 10A:
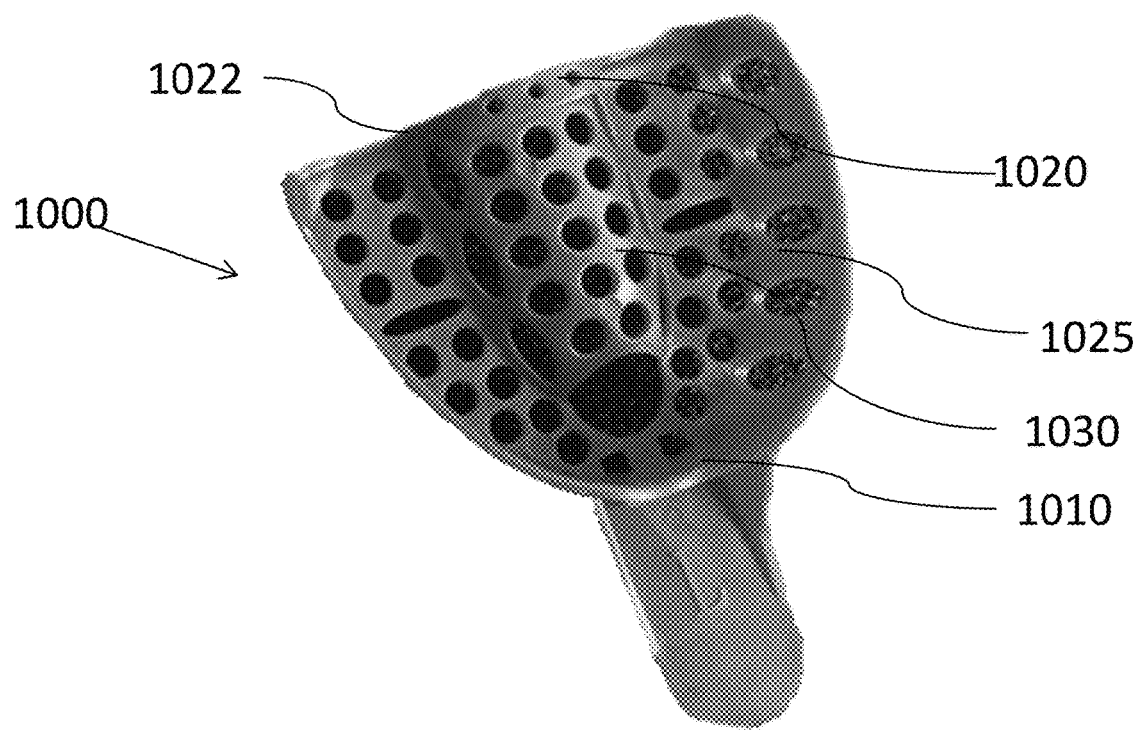
FIG. 10A is a top view of an impression tray.
Figure 10B:
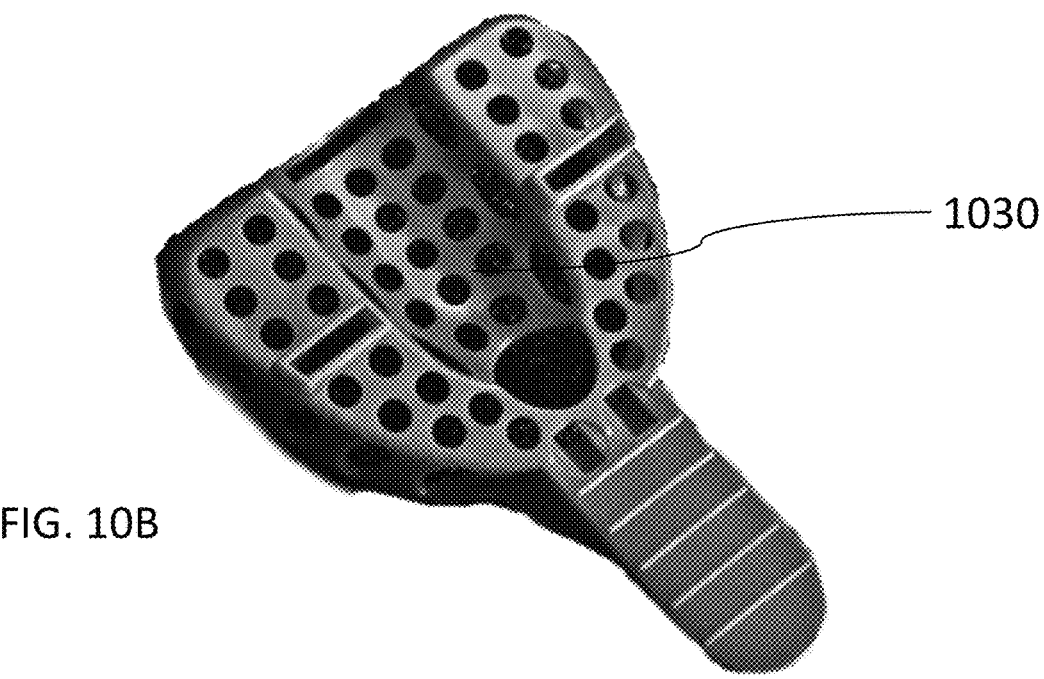
FIG. 10B is a bottom view of an impression tray, in accordance with certain embodiments.

In another configuration, a method comprises imaging an oral cavity of a human, printing an impression tray using the imaged oral cavity, using the printed impression tray and impression material to obtain an impression of the oral cavity of the human, and providing a removable oral device using the impression of the oral cavity. The removable oral device comprises a palatal element coupled to a clasping element, in which the palatal element is configured to contact a roof of a user's mouth at a palatal surface, and wherein the palatal element comprises a body comprising a thickness configured to lower a vaulted area of the roof of the mouth to decrease an overall oral volume of the mouth to a first oral volume. The clasping element, when present, is configured to assist in removal of the removable oral device from the mouth and/or to retain the palatal surface of the palatal element against the roof of the user's mouth when the removable oral device is inserted into the user's mouth. Conventional impression trays are generally one size fits all configurations and may not be suitable for producing the removable oral devices described herein. For example, the trays may be too large or not include suitable features to provide good impressions of the palatal surface of the user. In one example and referring to FIGS. 10A and 10B, an impression tray 1000 can be printed that includes a front surface 1010 and a back surface 1020 with a channel 1025 running between them in a generally semi-circular pattern which mirrors the upper teeth. The impression tray also comprises a raised central portion 1030 to capture the palatal shape of the user's mouth. The back surface 1020 comprises a stop or wall 1022 to prevent the molding material from pushing backwards into the user's mouth. This feature reduces the overall posterior side size of the removable oral device to avoid or deter the gagging reflex. Similarly, the front surface 1010 may comprise a wall to reduce the overall thickness of the removable oral device at the front to minimize or reduce lisping and/or to provide a palatal element which does not contact rear surfaces of the anterior teeth. Illustrative impression materials include those commonly used in dentistry applications, Silident materials, clays, polyvinylsiloxanes, alginates and other materials which can capture the shape of the upper mouth including the palate. The printed impression tray may also comprise the clasping element pre-printed to account for the space it takes up in the removable oral device. As shown in FIGS. 10A and 10B, the impression tray may comprise a plurality of apertures or holes to permit the impression material to be forced downward to provide a better representation of the palatal shape.

In certain examples, the method comprises using an image head configured to receive a disposable cover to image the oral cavity. In other embodiments, the method comprises injecting a material into the impression of the oral cavity to provide the removable oral device. In some examples, the method comprises using a gasket with the removable oral device, wherein the gasket is present between the body of the palatal element and the clasping element. In some examples, the method comprises three-dimensionally printing the impression tray using a photo-curable material. In other examples, the method comprises photo-curing the printed impression tray using UV/Visible light. In additional examples, the method comprises scanning the impression to provide a digital image of the impression. In other examples, the method comprises using the digital image to print the removable oral device. In some embodiments, the method comprises three-dimensionally printing the removable oral device from the digital image using an inkjet three-dimensional printer. In certain examples, the method comprises three-dimensionally printing the removable oral device from the digital image using digital light processing.

In certain instances, the impression tray can be used to assist in determining the shape of the clasping element, e.g., the shape of the supporting wires of the clasping element. In other examples, the impression tray may be configured with a stop or other feature at the front to guide shaping of the front portion of the palatal element in a manner that reduces lisping. For example, the impression tray may be configured to permit the removal of the entire front portion of the palatal element so the tongue can contact the back surfaces of the front teeth in order to reduce lisping. Similarly, the back portion of the impression tray can be designed to inhibit rear movement of the impression material so that a lower amount of material (or no material at all) is present at the back portion of the palatal element near the back of the mouth. Lesser amounts of the material, e.g., a reduced thickness, can reduce the likelihood of gagging when the removable oral device is in place.

In another configuration, a method comprises obtaining an impression of an oral cavity of a human using an impression tray and impression material, and providing a removable oral device using the impression of the oral cavity. In some instances, the removable oral device comprises a palatal element coupled to a clasping element, in which the palatal element is configured to contact a roof of a user's mouth at a palatal surface, the palatal element comprising a body comprising a thickness configured to lower a vaulted area of the roof of the mouth to decrease an overall oral volume of the mouth to a first oral volume, wherein the body comprises a variable hardness across a tongue surface of the body. The clasping element, when present, is configured to assist in removal of the removable oral device from the mouth and/or to retain the palatal surface of the palatal element against the roof of the user's mouth when the removable oral device is inserted into the user's mouth.

In certain examples, the variable hardness may provide several desirable attributes including, but not limited to, a better fit, a less obtrusive device, enhanced flexibility, reduced lisping and/or reduced gagging. In some examples, different materials are used at the edges of the palatal element to provide one or more of these desired attributes. In one example, an impression tray can be filled with a putty-like material, an alginate or other materials. As noted herein, the impression tray may include front and back features which permit the palatal element to be thinner at these areas, e.g., vertical stops or dams may be present to stop the putty material from entering into these spaces. While the exact putty material used can vary, vinyl polysiloxane materials or other suitable materials can be used. Both one-part and two-part impression materials can be used with one or more hardeners or other materials as desired. The impression tray typically comprises one or more bulges, e.g., bulge 1030 in FIGS. 10A and 10B, to permit palatal impression as well. In comparison to orthodontic molds, both the teeth and palatal surfaces are used for the impression. The impression tray may comprise holes in the bottom surfaces to permit excess material to be forced downward rather than forward or backward. If desired, the overall impression can be used in combination with one or more oral imaging methods to provide a combined image which can be used to provide a removable oral device. The combination of a digital image and a physical mold can permit further tuning of the removable oral device shape and/or size.

In another configuration, a method comprises imaging an oral cavity of a human using a first removable oral device comprising a palatal element coupled to a clasping element. For example, the palatal element of the first removable oral device comprises a body comprising an embedded camera configured to capture an image of the oral cavity. The clasping element of the first removable oral device is configured to place a palatal surface of the palatal element of the first removable oral device adjacent to a roof of the human's mouth when the first removable oral device is inserted into the human's mouth. Once properly placed, the palatal element can capture images of the mouth of the user and store them on a memory unit or other device on-board the removable oral device. The captured images can then be used to provide a second removable oral device comprising a palatal element coupled to a clasping element. The second removable oral device can be customized or tailored for the exact mouth shape and may include thinner front and rear sections to reduce lisping and gagging, respectively. The palatal element of the second removable oral device is configured to contact a roof of a user's mouth at a palatal surface. The palatal element of the second removable oral device comprises a body comprising a thickness configured to lower a vaulted area of the roof of the mouth to decrease an overall oral volume of the mouth to a first oral volume. The clasping element, when present, is configured to assist in removal of the removable oral device from the mouth and/or to retain the palatal surface of the palatal element against the roof of the user's mouth when the removable oral device is inserted into the user's mouth. If desired, the camera can be replaced with an ultrasound sensor, optical sensor or other sensors which can sense the distance of the sensor to various areas of the palate or roof of the mouth. These distance measurements can be used to provide a digital image of the mouth, which can be used to provide the removable oral device.

In certain instances, a method of producing a removable oral device comprises providing a removable oral device comprising a palatal element coupled to a clasping element. The palatal element is configured to contact a roof of a user's mouth at a palatal surface and comprises a body comprising a thickness configured to lower a vaulted area of the roof of the mouth to decrease an overall oral volume of the mouth to a first oral volume. The palatal element comprises a softer material at edges of the body than at an apex of the body, e.g., the palatal element may comprise a variable hardness. The clasping element, when present, is configured to assist in removal of the removable oral device from the mouth and/or to retain the palatal surface of the palatal element against the roof of the user's mouth when the removable oral device is inserted into the user's mouth. The method also comprises forming the clasping element by bending the clasping element and sizing it to contact outer surfaces of at least three adjacent teeth, e.g., adjacent teeth with tooth numbers 1 to 4 or 12 to 16 or both where two clasping elements are present.

In certain examples, the method comprises configuring the body to be thinner at a front surface of the body than at the apex surface. In some examples, the method comprises configuring the body to be thinner at a rear surface of the body than at the apex surface. In other examples, the method comprises configuring the clasping element as a pair of wires with one wire positioned on each side of the palatal element. In additional examples, the method comprises configuring the wires to have a smaller outer diameter at a terminus of the wires. In some embodiments, the method comprises configuring the removable oral device to not alter a position of the user's teeth. In other examples, the method comprises configuring the removable oral device to not retain a position of the user's teeth. In some instances, the method comprises sizing the clasping element to contact outer surfaces of tooth numbers 1 to 5 or tooth numbers 1 to 3 or tooth numbers 1 to 2 or tooth numbers 2 to 4 or tooth numbers 2 to 3 or tooth numbers 11 to 16 or tooth numbers 13 to 16 or tooth numbers 14 to 16 or tooth numbers 13 to 15 or tooth numbers 13 to 14.

In certain embodiments, the methods described herein may use one or more computer systems and/or common hardware circuity including, for example, a microprocessor and/or suitable software for operating the system, e.g., to obtain an image, print some portion of a removable oral device, etc. In some examples, the printer may comprise a processor, operating system and other features to print a removable oral device. Similarly, a scanner configured to scan the oral cavity may comprise one or more of these features. The processor can be integral to the systems which implement the method or may be present on one or more accessory boards, printed circuit boards or computers electrically coupled to the components of the methods. The processor can be used, for example, to receive and/or process images from the mouth, control printing operations and the like. The processor is typically electrically coupled to one or more memory units to receive data from the other components of the system and permit adjustment of the various system parameters as needed or desired. The processor may be part of a general-purpose computer such as those based on Unix, Intel PENTIUM-type processor, Motorola PowerPC, Sun UltraSPARC, Hewlett-Packard PA-RISC processors, or any other type of processor. One or more of any type computer system may be used according to various embodiments of the technology. Further, the system may be connected to a single computer or may be distributed among a plurality of computers attached by a communications network. It should be appreciated that other functions, including network communication, can be performed and the technology is not limited to having any particular function or set of functions. Various aspects of the methods may be implemented as specialized software executing in a general-purpose computer system. The computer system may include a processor connected to one or more memory devices, such as a disk drive, memory, or other device for storing data. Memory is typically used for storing programs, calibrations and data during operation of the imaging system, printing system or other systems which implement the methods. Components of the computer system may be coupled by an interconnection device, which may include one or more buses (e.g., between components that are integrated within a same machine) and/or a network (e.g., between components that reside on separate discrete machines). The interconnection device provides for communications (e.g., signals, data, instructions) to be exchanged between components of the system. The computer system typically can receive and/or issue commands within a processing time, e.g., a few milliseconds, a few microseconds or less, to permit rapid control of the devices which implement the methods. For example, computer control can be implemented to control the rate at which the various layers of the palatal element are printed. The processor typically is electrically coupled to a power source which can vary, for example, be a direct current source, an alternating current source, a battery, a fuel cell or other power sources or combinations of power sources. The power source can be shared by the other components of the system including any wireless probes or devices used. The system may also include one or more input devices, for example, a keyboard, mouse, trackball, microphone, touch screen, manual switch (e.g., override switch) and one or more output devices, for example, a printing device, display screen, speaker. In addition, the system may contain one or more communication interfaces that connect the computer system to a communication network (in addition or as an alternative to the interconnection device). The system may also include suitable circuitry to convert signals received from the various electrical devices present in the systems. Such circuitry can be present on a printed circuit board or may be present on a separate board or device that is electrically coupled to the printed circuit board through a suitable interface, e.g., a serial ATA interface, ISA interface, PCI interface or the like or through one or more wireless interfaces, e.g., Bluetooth, Wi-Fi, Near Field Communication or other wireless protocols and/or interfaces.

In certain embodiments, the storage system used in implementing the methods typically includes a computer readable and writeable nonvolatile recording medium in which codes can be stored that can be used by a program to be executed by the processor or information stored on or in the medium to be processed by the program. The medium may, for example, be a disk, solid state drive or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in the storage system or in the memory system. The processor generally manipulates the data within the integrated circuit memory and then copies the data to the medium after processing is completed. For example, the processor may receive images from a probe and use them to provide three-dimensional coordinates representative of the user's oral cavity. A variety of mechanisms are known for managing data movement between the medium and the integrated circuit memory element and the technology is not limited thereto. The technology is also not limited to a particular memory system or storage system. In certain embodiments, the system may also include specially-programmed, special-purpose hardware, for example, an application-specific integrated circuit (ASIC) or a field programmable gate array (FPGA). Aspects of the technology may be implemented in software, hardware or firmware, or any combination thereof. Further, such methods, acts, systems, system elements and components thereof may be implemented as part of the systems described above or as an independent component. Although specific systems are described by way of example as one type of system upon which various aspects of the technology may be practiced, it should be appreciated that aspects are not limited to being implemented on the described system. Various aspects may be practiced on one or more systems having a different architecture or components. The system may comprise a general-purpose computer system that is programmable using a high-level computer programming language. The systems may be also implemented using specially programmed, special purpose hardware. In the systems, the processor is typically a commercially available processor such as the well-known Pentium class processors available from the Intel Corporation. Many other processors are available. Such a processor usually executes an operating system which may be, for example, the Windows 95, Windows 98, Windows NT, Windows 2000 (Windows ME), Windows XP, Windows Vista, Windows 7, Windows 8 or Windows 10 operating systems available from the Microsoft Corporation, MAC OS X, e.g., Snow Leopard, Lion, Mountain Lion or other versions available from Apple, the Solaris operating system available from Sun Microsystems, or UNIX or Linux operating systems available from various sources. Many other operating systems may be used, and in certain embodiments a simple set of commands or instructions may function as the operating system.

In certain examples, the processor and operating system may together define a platform for which application programs in high-level programming languages may be written. It should be understood that the technology is not limited to a particular system platform, processor, operating system, or network. Also, it should be apparent to those skilled in the art, given the benefit of this disclosure, that the present technology is not limited to a specific programming language or computer system. Further, it should be appreciated that other appropriate programming languages and other appropriate systems could also be used. In certain examples, the hardware or software can be configured to implement cognitive architecture, neural networks or other suitable implementations. If desired, one or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

In some instances, various embodiments may be programmed using an object-oriented programming language, such as, for example, SQL, SmallTalk, Basic, Java, Javascript, PHP, C++, Ada, Python, iOS/Swift, Ruby on Rails or C# (C-Sharp). Other object-oriented programming languages may also be used. Alternatively, functional, scripting, and/or logical programming languages may be used. Various configurations may be implemented in a non-programmed environment (e.g., documents created in HTML, XML or other format that, when viewed in a window of a browser program, render aspects of a graphical-user interface (GUI) or perform other functions). Certain configurations may be implemented as programmed or non-programmed elements, or any combination thereof. In some instances, the methods can be implemented through a remote interface such as those present on a mobile device, tablet, laptop computer or other portable devices which can communicate through a wired or wireless interface and permit implementation of the methods remotely if desired.

In certain embodiments, the impressions of the palatal area of a user can be used to build up a palatal element using various layers of material. For example, a first material comprising an acrylate can be placed into the mold and built up to a desired thickness. A second material, typically also comprising an acrylate, can be placed into the mold at the edges and coupled to the first material by permitting the various materials to bond to each other or optionally by using a suitable cross-linking material. Once coupled to each other, there generally is no interface between the first material and the second material. Similar materials (acrylate+cross-linking material) can be used to build up the material around any clasping elements. As noted herein, the second material placed at the edges may be selected to soften at body temperature. Each of the first material and the second material used with the mold to provide the removable oral device may independently be selected as an acrylate, a methacrylate, an acrylic polymer and co-polymer, Silident, a functionalized bisphenol A methacrylate such as a monofunctional bisphenol A dimethacrylate or a difunctional bisphenol A dimethacrylate, a diglycidyl methacrylate ester of bisphenol-A or a bisphenol-A diglycidyl ether and other materials. In some examples, the molded palatal element of the removable oral device may comprise one or more of ethylene glycol dimethacrylate, diethylene glycol dimethacrylate, triethylene glycol dimethacrylate, polyethylene glycol dimethacrylate, 2,2 bis[4-(methacryloxy ethoxy)phenyl]propane, tricyclodecane dimethanol dimethacrylate, 1,10-decanediol dimethacrylate, 1,6-hexanediol dimethacrylate, 1,9-nonanediol dimethacrylate, neopentyl glycol dimethacrylate, 2-hydroxy 1-3 dimethacryloxy propane, trimethylolpropane trimethacrylate, ethoxylated trimethylol propane trimethacrylate, ditrimethyolpropane tetramethacrylate, tris (2-hydroxy ethyl)isocyanurate trimethacrylate, dipentaerythritol pentamethacrylate, ethoxylated pentaerythritol tetramethacrylate, propoxylated glyceryl trimethacrylate, propoxylated trimethylolpropane trimethacrylate, and a polyester dendrimer.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A method of producing a removable oral device, the method comprising:
    obtaining an image of an oral cavity of a human; and
    providing the removable oral device using the obtained image, the removable oral device comprising a palatal element coupled to a clasping element, in which the palatal element is configured to contact a roof of the human's mouth at a palatal surface, the palatal element comprising a body comprising a thickness configured to lower a vaulted area of the roof of the mouth to decrease an overall oral volume of the mouth to a first oral volume, wherein the body comprises a variable hardness across a tongue surface of the body, wherein the variable hardness comprises a Vickers hardness that gradually decreases from a central apex to outer edges of the palatal element, wherein the clasping element is configured to assist in removal of the removable oral device from the mouth, and wherein the removable oral device is configured to not alter or retain a position of teeth with continued use of the removable oral device.

2. The method of claim 1, further comprising using an impression tray in combination with the obtained image of the oral cavity to provide a composite image.

3. The method of claim 2, further comprising printing the palatal element of the removable oral device from the composite image using a three-dimensional printer.

4. The method of claim 1, wherein areas of the palatal element adjacent to the clasping element are softer than other areas of the body.

5. The method of claim 4, wherein a Vickers hardness at the areas adjacent to the clasping element are at least 5× less hard than a hardness of other areas of the body.

6. The method of claim 1, wherein the clasping element comprises a first wire positioned adjacent to tooth numbers 1-4 and a second wire positioned adjacent to tooth numbers 13-16.

7. The method of claim 6, wherein the first wire and the second wire each comprises a material so the first and second wire do not directly contact the teeth.

8. The method of claim 6, wherein the first wire is connected to the second wire in the body of the palatal element.

9. The method of claim 1, further comprising printing the palatal element of the removable oral device using a three-dimensional printer.

10. The method of claim 1, further comprising bending the clasping element so the clasping element contacts an outer surface of at least one tooth.

11. The method of claim 1, wherein the clasping element comprises a wire on each side of the palatal element.

12. The method of claim 1, wherein the body comprises a different material at areas adjacent to the clasping element.

13. The method of claim 1, further comprising cross-linking a material in the body by sprinkling a cross-linker on the body.

14. The method of claim 1, further comprising smoothing the palatal element to prevent food from sticking to the palatal element.

15. The method of claim 1, further comprising printing the palatal element and the clasping element of the removable oral device using a three-dimensional printer.

* * * * *